(12) United States Patent
Kuper et al.

(10) Patent No.: US 7,985,433 B2
(45) Date of Patent: Jul. 26, 2011

(54) METHOD FOR THE PRODUCTION OF A PLANT-BASED MEDICAMENT

(75) Inventors: Willi Kuper, Gross-Rohrheim (DE); Wulf Becker, Ober-Ramstadt (DE)

(73) Assignee: Steigerwald Arzneimittelwerk GmbH (DE)

( * ) Notice: Subject to any disclaimer, the term of this patent is extended or adjusted under 35 U.S.C. 154(b) by 7 days.

(21) Appl. No.: 12/459,009

(22) Filed: Jun. 25, 2009

(65) Prior Publication Data

US 2009/0324755 A1 Dec. 31, 2009

(30) Foreign Application Priority Data

Jun. 26, 2008 (DE) .......................... 10 2008 002 685

(51) Int. Cl.
*A61K 36/00* (2006.01)
*A61K 36/236* (2006.01)
*A61K 36/28* (2006.01)
*A61K 36/232* (2006.01)
*A61K 36/534* (2006.01)
*A61K 36/48* (2006.01)

(52) U.S. Cl. ........ 424/725; 424/747; 424/757; 424/764; 424/773; 424/774; 424/777

(58) Field of Classification Search ........................ None
See application file for complete search history.

(56) References Cited

U.S. PATENT DOCUMENTS 5,618,537 A * 4/1997 Okpanyi ........................ 424/745

FOREIGN PATENT DOCUMENTS

EP 0 550 703 B1 7/1993

OTHER PUBLICATIONS

Schneider, Bitter candytuft (Iberis amara L.) finding of donors of valuable characteristics by collection and evaluation of wild accessions and the first steps for introduction into cultivation Bittere Schleifenblume, Zeitschrift fur Arznei- & Gewurzpflanzen, (2006) vol. 11, No. 3, pp. 133-141.*
Melzer et al, Meta-analysis: phytotherapy of functional dyspepsia with the herbal drug preparation STW 5 (Iberogast), Aliment Pharmacol Ther 2004; 20: 1279-1287.*
Kroll U., Crodes C.: Pharmaceutical prerequisites for a multi-target therapy. Phytomedicine 13 SV 12-19; ISSN: 0944-7113, 2006.
Wegener T., Wagner H.: The active components and the pharmacological multi-target principle of STW 5 (Iberogast®). Phytomedicine 13(2006), SV 20-35; ISSN: 0944-7113.
Saller R. et al.: Iberogast®. Eine modern phytotherapeutische Arzneimittelkombination zur Behandlung funkioneller Erkrankungen des Magen-Darm-Trakts (Dyspepsie, Colon irrabile)—von der Pflanzenheikunde zur Evidence Based Phytotherapy >>. Forsch Komplementärmed Klass Naturheilkd 2002; 9 (suppl 1): 1-20; ISBN: 3-8055-7462-2.
v. Czetsch-Lindenwald H: Pflanzliche Arzneizubereitungen; Süddeutsche Apotheker-Zeitung, Stuttgart, 2. Aufl. 1945, S. 73-75, 83, 247-251.
European Pharmacopoeia 7.0, "Herbal Drugs", Jul. 2010:1433, p. 676-677.
European Pharmacopoeia 7.0, "Extracts", Apr. 2008:0765, p. 674-676.

* cited by examiner

*Primary Examiner* — Qiuwen Mi
(74) *Attorney, Agent, or Firm* — Wood, Phillips, Katz, Clark & Mortimer

(57) ABSTRACT

A method for the production of a plant-based medicament which contains *Iberis amara*, Menthae piperitae folium, Matricariae flos, Carvi fructus, Melissae folium, Angelicae radix, Liquiritiae radix, Cardui mariae fructus and Chelidonii herba in the form of alcoholic extracts and a medicament produced according to this method, and its use.

27 Claims, 2 Drawing Sheets

METHOD FOR THE PRODUCTION OF A PLANT-BASED MEDICAMENT

BACKGROUND OF THE INVENTION

1. Field of the Invention

The present invention relates to a method for the production of a plant-based medicament which contains *Iberis amara*, Menthae piperitae folium, Matricariae flos, Carvi fructus, Mellissae folium, Angelicae radix, Liquiritiae radix, Cardui mariae fructus and Chelidonii herba in the form of alcoholic extracts, and a medicament produced by this method, and its use.

2. Background Art

Iberogast is a plant-based medicament (herbal combination preparation, phytopharmaceutical product), which is used for the treatment of functional dyspepsia and in gastrointestinal multitarget therapy. It has both a tonus-increasing effect in relaxed smooth musculature and also has a spasmolytic effect in paroxysmal states of the smooth musculature. The active pharmaceutical ingredients of this phytopharmaceutical product are preparations of fresh plants and herbal drugs, (dried plants or parts of plants) as ethanolic, liquid extracts. Iberogast contains extracts of *Iberis amara* (bitter candytuft), Menthae piperitae folium (peppermint leaves), Matricariae flos (chamomile flowers), Carvi fructus (caraway fruit), Melissae folium (lemon balm leaves), Angelicae radix (angelica root), Liquiritiae radix (liquorice root), Cardui mariae fructus (milk thistle fruit) and Chelidonii herba (celandine).

European Patent EP 0550 703 B1 already describes a plant-based medicament with a limited number of 6 extracts.

Iberogast itself, which comprises 9 extracts, is a medicament which has been well-established for years. The pharmaceutical quality of the extracts has a decisive influence on the effectiveness and harmlessness of herbal medicaments. In addition to complying with specifications of the initial drugs in accordance with the pharmacopeia, the reproducibility of the production processes (validation) is the essential prerequisite for the high standard as German and European phtyopharmaceutical product. Based on the new guidelines, which also apply to herbal medicaments in relation to the respective European regulations, there is an obligation to be consistent with the information regarding content which is declared for the respective medicament. Deviation from this information may only be ±5% of the declared content of the ingredients which determine effectiveness (lead substance, active marker or analytical marker substance).

It has proved to be problematic to obtain a constant effective substance content in the finished medicament Iberogast and to obtain a consistent, reproducible quality. Corresponding investigations with regard to the pharmaceutical development indicated precipitations/crystal formation in the extract of angelica root, which led to inhomogeneities in the production batch and consequently led to unacceptable fluctuations of the osthol content (lead substance). On the one hand, the recovery rate of the osthol content increased in the first weeks after the first analysis in clear-filtered solutions, and on the other hand the total content decreased in production batches in accordance with the sediment formation.

SUMMARY OF THE INVENTION

It is therefore an object of the present invention to make possible a constant effective substance content in the finished medicament with a consistent, reproducible quality in the final package over a longer period of time.

DETAILED DESCRIPTION OF THE PREFERRED EMBODIMENT

Figure 1:
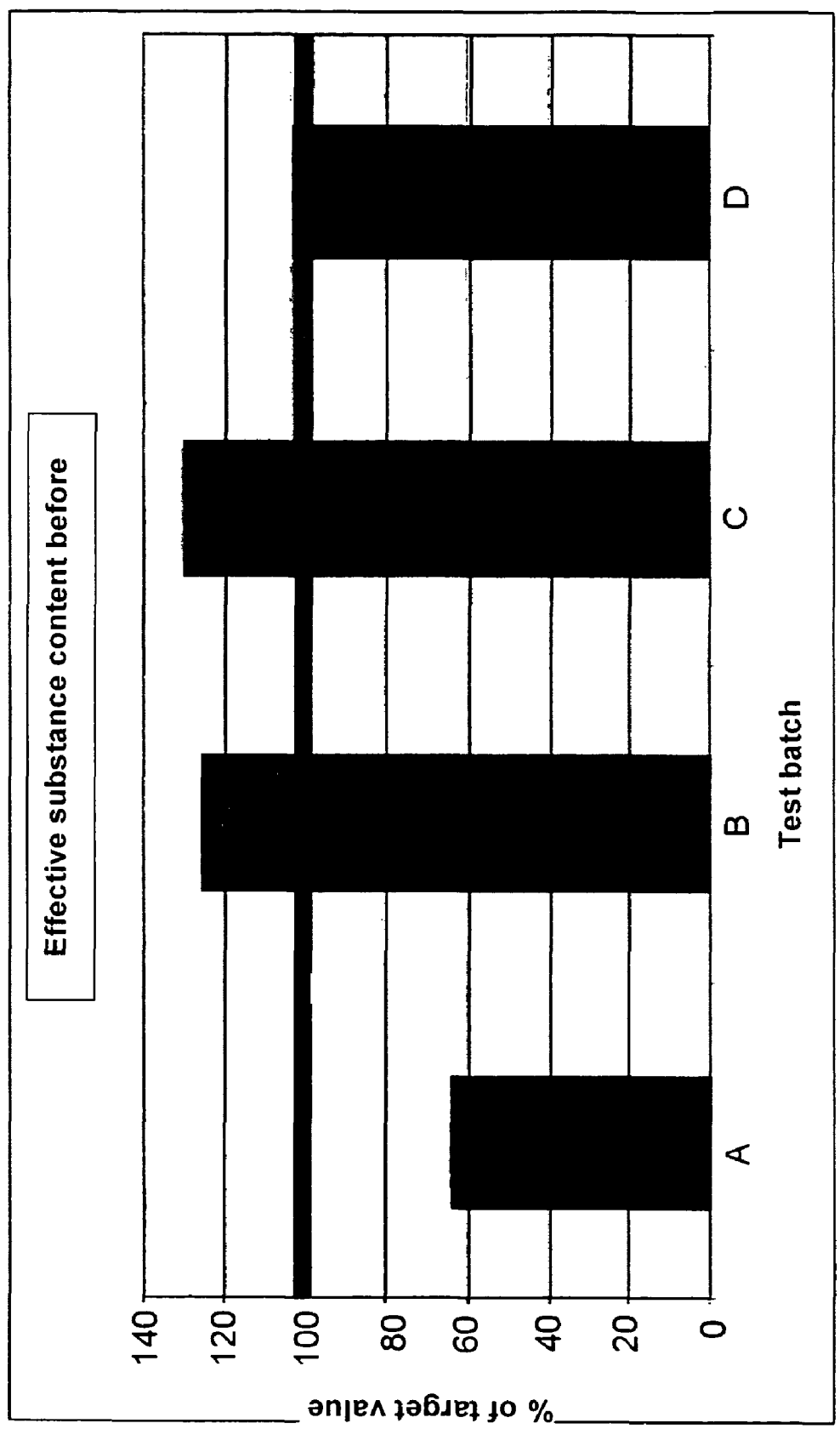
FIG. 1 shows the recovery rate of the lead substance osthol indicated in % of the target value in the finished product. A recovery rate of 100% means that all osthol, which had been present in the initial Angelicae radix drug extract, is also present in the finished product. A recovery rate between 95 and 105% is mandatory (range of 95 to 105% is indicated as black area in the Fig.). Test batches A, B, C and D were all prepared using arbitrary mixing sequences. Only test batch D meets the criteria of having a recovery rate between 95 and 105%. Test batches A, B and C, which were also prepared according to other arbitrary mixing sequences fail.

To address the above problems, a method is practiced for the production of a plant-based medicament which contains *Iberis amara*, Menthae piperitae folium, Matricariae flos, Carvi fructus, Mellissae folium, Angelicae radix, Liquiritiae radix, Cardui mariae fructus and Chelidonii herba in the form of alcoholic extracts, wherein in a first step a) Angelicae radix extract and Liquiritiae radix extract are mixed together in a volume ratio of 1:6 to 3:1 and then in at least one further step the mixture of step a) is added together with the extracts of the further ingredients or mixtures containing them, which are produced separately and if applicable once again contain Liquiritae radix.

With the background of the problem which is posed, a range of process methods and also analytical methods were investigated or specifically developed. In particular, the volatile components of the drugs with etheric oils and the precipitations/crystal formation in the extract of angelica root led to non-reproducible quality fluctuations. Surprisingly, only the use of a production method according to Claim 1 emerged as being effective. A crucial factor here is the sequence of additions of the individual drug extracts. A preferred variant of the method according to the invention for the production of a plant-based medicament is characterized in that in a step b) a mixture is produced containing extracts of Matricariae flos, *Iberis amara* and Carvi fructus, the mixture of step a) is added to this and in a step c) extracts of Cardui mariae fructus, Menthae piperitae folium, Melissae folium and Chelidonii herba are added. Step a) is as defined above, i.e. Angelicae radix extract and Liquiritiae radix extract are mixed together in a volume ratio of 1:6 to 3:1.

It is to be assumed that the saponins of the liquorice extract stabilize the osthol in the angelica extract and that they subsequently emulsify the etheric oils of the predominantly oleiferous drugs (chamomile, *Iberis amara* and caraway). In addition, it is presumed that the mucilaginous drugs such as milk thistle prevent the sedimentation (milk thistle, mint, lemon balm). The mixing sequence (addition sequence) prevents the formation of crystals of the ingredients (secondary plant substances) of the herb extracts. The crystal formation affects the batch homogeneity. Therefore, the addition sequence according to the invention ensures a reproducible production of the product.

In each case, single extracts are used. Compared with multiple extracts, the mixture of single extracts has the advantage that for the respective drugs and fresh plants, optimum extractants and extraction conditions can be selected, and the ingredients which determine the effectiveness or are pharmaceutically relevant are thus present in a good yield. The transition rates of the ingredients and those of the extractive substance yields of the drug which is used are traceable, which is of great importance for the analysis.

Preferably, in the method according to the invention for the production of a plant-based medicament, mixtures containing extracts of Menthae piperitae folium, Carvi fructus and Melissae folium; Cardui mariae fructus and Matricariae flos; and *Iberis amara* and Chelidonii herba are produced separately.

In particular, it is preferred that Angelicae radix extract and Liquiritiae radix extract are mixed together in step a) in a volume ratio of 1:2 to 2:1. In a particularly preferred embodiment of the method according to the invention, Angelicae radix extract and Liquiritiae radix extract are mixed together in step a) in a volume ratio of 1:1.

Proceeding from the initial mixing of Angelicae radix extract and Liquiritiae radix extract in step a), different variants of the further mixture have surprisingly proved to be particularly suitable.

A preferred embodiment of the production method according to the invention is based on the fact that in a step b) the mixture of step a) is mixed together with a mixture containing extracts of Menthae piperitae folium, Carvi fructus and Melissae folium, in a step c) a mixture containing extracts of Cardui mariae fructus and Matricariae flos is added and in a step d) the addition takes place of a mixture containing extracts of Iberis amara and Chelidonii herba.

A likewise preferred embodiment is characterized in that in a step b) the mixture of step a) is mixed together with a mixture containing extracts of Menthae piperitae folium, Carvi fructus and Melissae folium, in a step e) a mixture containing extract of Cardui mariae fructus and Matricariae flos with a mixture containing extracts of *Iberis amara* and Chelidonii herba are mixed together and in a step f) the mixtures of steps b) and e) are mixed together.

Based on an initial mixture of Angelicae radix extract and Liquiritiae radix extract in step a) in a volume ratio of 1:6 to 3:1, it has likewise proved to be preferred to additionally add a particular proportion of the Liquiritiae radix extract in a later step. Accordingly, a preferred embodiment of the present invention is characterized in that the mixture containing Menthae piperitae folium extract, Carvi fructus extract and Melissae folium extract additionally contains Liquiritiae radix extract. It is particularly preferred here if the mixture containing Menthae piperitae folium extract, Carvi fructus extract and Melissae folium extract additionally contains Liquiritiae radix extract, wherein the volume of the containing Liquiritiae radix extract is in the ratio 1:1 to the volume of Liquiritiae radix extract contained in the mixture of Angelicae radix extract and Liquiritiae radix extract from step a).

According to the invention, the production method is directed to the production of a plant-based medicament, which comprises 15 to 40 vol. % *Iberis amara*,
5 to 30 vol. % Menthae piperitae folium,
20 to 40 vol. % Matricariae flos,
10 to 30 vol. % Carvi fructus,
10 to 30 vol. % Melissae folium,
5 to 30 vol. % Angelicae radix,
10 to 30 vol. % Liquiritiae radix,
5 to 30 vol. % Cardui mariae fructus and
5 to 30 vol. % Chelidonii herba in the form of alcoholic extracts. The method is preferably directed to the production of a plant-based medicament, which comprises 15 vol. % *Iberis amara*,
5 vol. % Menthae piperitae folium,
20 vol. % Matricariae flos,
10 vol. % Carvi fructus,
10 vol. % Melissae folium,
10 vol. % Angelicae radix,
10 vol. % Liquiritiae radix,
10 vol. % Cardui mariae fructus and
10 vol. % Chelidonii herba in the form of alcoholic extracts.

It is preferred to use extracts from fresh plants or drug extracts. In particular, it is to be preferred if the *Iberis amara* extract is a fresh plant extract of *Iberis amara* totalis (flowers, leaves, stem and roots). The harvesting of *Iberis amara* fresh plant with flowers, leaves, stem, roots takes place at a time at which the content of flavonoids has reached its optimum. Within the framework of flavonoids, the glycosides of kaempferol are particularly relevant as antiphlogistics. The extract of the fresh plant contains, as the most important flavonoid, kaempferol-3,4'-di-O-β-glucopyranoside-7-O-α-rhamnopyranoside. The fresh plant preferably contains at least 100 μg/g flavonoids, in particular kaempferol-3,4'-di-O-β-glucopyranoside-7-O-α-rhamnopyranoside. With regard to the *Iberis amara* fresh plant extract, it is preferred if this has a flavonoid content of kaempferol-3,4'-di-O-β-glucopyranoside-7-O-α-rhamnopyranoside of 0.05 to 0.2 mg/ml.

The plant material according to the invention additionally contains a limited content of cucurbitacins, in particular cucurbitacin I and E. The fresh plant preferably contains a content of cucurbitacin I of a maximum of 500 μg/g and a content of cucurbitacin E of likewise a maximum of 500 μg/g. Higher values are not desired, because after a certain threshold value, these substances have a side-effect potential. With regard to the extract, it is preferred that the *Iberis amara* extract is a fresh plant extract which has a content of cucurbitacins of 0 to 200 μg/ml. It is particularly preferred here if the *Iberis amara* extract is a fresh plant extract which has a content of cucurbitacins of 35 to 185 μg/ml. In particular, it is to be preferred that the *Iberis amara* extract is a fresh plant extract which has a content of cucurbitacin I of 0 to 100 μg/ml and a content of cucurbitacin E of 0 to 100 μg/ml.

As already mentioned, extracts from fresh plants or drug extracts can be used. Preferably, the method according to the invention is characterized in that the extracts of Menthae piperitae folium, Matricariae flos, Carvi fructus, Melissae folium, Angelicae radix, Liquiritiae radix, Cardui mariae fructus and Chelidonii herba are drug extracts.

With regard to the fresh plant extract of *Iberis amara* totalis, it is to be preferred that the ratio of macerated/percolated plant to the extract is between 1 gram:10 ml (10 gram) and 1 gram:1 ml (1 gram). In particular, it is preferred that with the fresh plant extract, the ratio of macerated/percolated plant to the extract is from 1 gram:1.5 ml (1.5 gram) to 1 gram:2.5 ml (2.5 gram).

Preferably, with the drug extracts the ratio of drugs to the extract is from 1 gram:1 ml (1 gram) to 1 gram:10 ml (10 gram). It is particularly preferred here if with the drug extracts the ratio of drugs to the extract is from 1 gram:2 ml (2 gram) to 1 gram:4 ml (4 gram). In a preferred embodiment, the ratio in the case of drug extracts of drugs to the extract is from 1 gram:2.5 ml (2.5 gram) to 1 gram:3.5 ml (3.5 gram).

The preferred extractant comprises water and aqueous ethanol with a concentration of 0.1 to 60 vol. % ethanol. Particularly preferably, the extractant comprises aqueous ethanol with a concentration of 30 to 50 vol. % ethanol. In a preferred embodiment, the extractant for the fresh plant extract is aqueous ethanol with a concentration of 50 vol. % ethanol and the extractant for the drug extracts is aqueous ethanol with a concentration of 30 vol. % ethanol.

The present invention also comprises a plant-based medicament which was produced by the method according to the invention.

Likewise, the present invention comprises the use of this plant-based medicament for the treatment of disorders of the gastrointestinal tract, in particular for the treatment of functional dyspepsia.

Furthermore, the use of the plant-based medicament is preferred for the inhibition of gastric juice production, and the use for the treatment of ulcers.

The medicament is preferably used as an anti-inflammatory and/or anti-phlogistic. Likewise, the use as antioxidant and/or radical scavenger is preferred.

A further preferred use is constituted by the usage of the medicament according to the invention as a modulator of gastrointestinal mobility.

Figure 2:
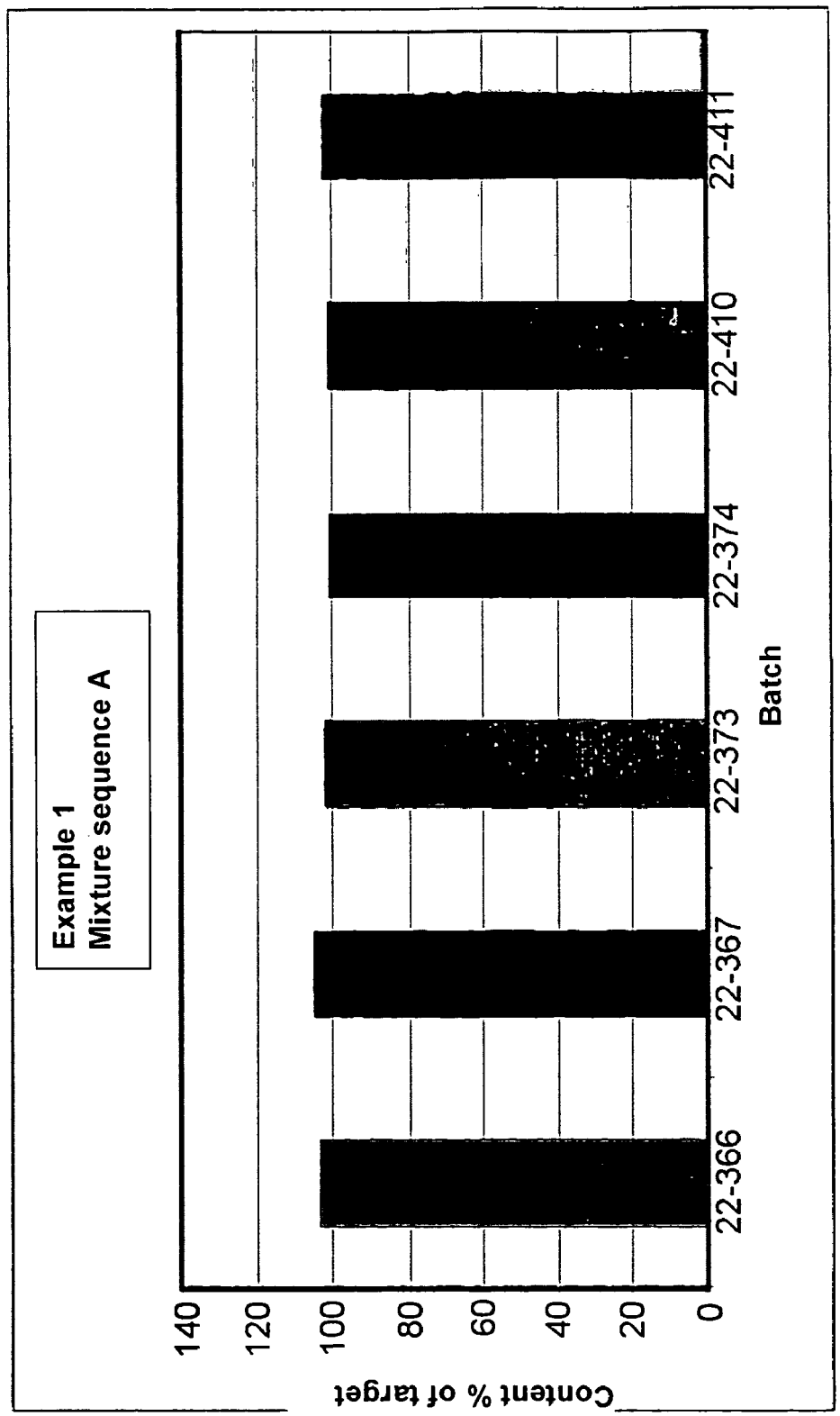
FIG. 2 shows the recovery rate of the lead substance osthol indicated in % of the target value in the finished product. A recovery rate of 100% reflects that all osthol, which has been present in the initial Angelicae radix drug extract, is also present in the finished product. A recovery rate between 95 and 105% is mandatory. All six batches, which are graphically represented in FIG. 2, were prepared according to Example 1, i.e., according to the mixing sequence A. The numbers 22-366, . . . , 22-411 are sample numbers. All batches meet the criteria of having a recovery rate between 95 and 105%. The same results were obtained using a mixing sequence according to Example 2 (sequence B) and according to Example 3 (sequence C). Thus, the results of Examples 2 and 3 were not represented separately.

The crystal formation is significantly inhibited when the mixture sequence according to the invention is adhered to. Without adhering to this sequence, the content values for osthol lie far outside the permissible tolerance both in the angelica drug extract and also in the finished product, i.e. the recovery of the lead substance osthol did not lie in the range of 95 to 105% of the target value. The batches produced with adherence to the mixture sequence according to the invention no longer had any deviations. Likewise, it can be seen that when the sequence is adhered to, scarcely any crystal formation is to be observed. For example, FIGS. 1 and 2 show the batch homogeneity with regard to the examined plant ingredient (osthol) with an arbitrary sequence (FIG. 1) and with the mixture sequence according to the invention of the individual herb extracts in accordance with Examples 1, 2 and 3 (FIG. 2). The examples 1, 2 and 3 according to the invention did not show any appreciable differences, so that a separate representation was dispensed with.

The invention is further explained below with the aid of examples. For clarification, nomenclature as used in the claims and examples, is cross-referenced below.

| | |
|---|---|
| candytuft | *Iberis amara* |
| peppermint leaf | *Menthae piperitae folium* |
| chamomile | *Matricariae flos* |
| caraway | *Carvi fructus* |
| lemon balm | *Melissae folium* |
| milk thistle fruit | *Cardui mariae fructus* |
| celandine | *Chelidonii herba* |

EXAMPLES

| Production formula | | |
|---|---|---|
| Ingredients | Amount in g | Amount in ml |
| Drug extract of chamomile flowers (1:2-4) | 1980 | 2000 |
| Fresh plant extract of bitter candytuft (1:1.5-2.5) | 1455 | 1500 |
| Drug extract of caraway (1:2.5-3.5) | 975 | 1000 |
| Mixture of drug extract of liquorice root (1:2.5-3.5) | 990 | 1000 |
| Drug extract of *angelica* root (1:2.5-3.5) | 990 | 1000 |
| Drug extract of milk thistle fruit (1:2.5-3.5) | 970 | 1000 |
| Drug extract of peppermint leaves (1:2.5-3.5) | 495 | 500 |
| Drug extract of lemon balm leaves (1:2.5-3.5) | 990 | 1000 |
| Drug extract of celandine (1:2.5-3.5) | 990 | 1000 |

Extractant for *Iberis amara*: ethanol 50% (V/V)
Extractant for all other drug extracts: ethanol 30% (V/V)

The individual ingredients must be mixed homogeneously before weighing. The ingredients are weighed in and mixed successively according to the production formula into high-grade steel and plastic containers.

Example 1

Sequence A

Pre-mixture: A pre-mixture of liquorice root extract and angelica root extract is produced in the ratio 1:1. The ingredients are weighed in successively and mixed according to the production formula.

Final mixture: The ingredients peppermint leaf drug extract, caraway drug extract and lemon balm drug extract are mixed. The pre-mixture is then added to this. The ingredients chamomile drug extract and milk thistle drug extract, and also celandine drug extract and the fresh plant extract candytuft are weighed in to this. The extracts are mixed.

Example 2

Sequence B

Pre-mixture: Angelica root extract and liquorice root extract are mixed 1:1.

Final mixture: The ingredients peppermint leaf drug extract, caraway drug extract and lemon balm drug extract are mixed. Added to this mixture is the mixture of angelica root extract and liquorice root extract. A mixture of milk thistle fruit drug extract and chamomile drug extract is produced separately with a mixture of celandine drug extract and fresh plant extract candytuft. The mixtures are finally mixed together.

Example 3

Sequence C

Pre-mixture: A pre-mixture of liquorice root extract and angelica root extract is produced in the ratio 1:2 (1 part:2 parts). The ingredients are weighed in successively and mixed according to the production formula.

Final mixture: A further part of liquorice root extract is mixed together with peppermint leaf drug extract, lemon balm leaf drug extract and caraway drug extract. The obtained mixture is mixed with the pre-mixture. Chamomile drug extract and milk thistle drug extract and also fresh plant extract candytuft and celandine drug extract are then added.

The obtained solutions of Examples 1, 2 and 3 are stored in high-grade steel or plastic tanks at room temperature (15-25° C.) for at least 14 days (including the storing and retrieval days).

The osthol content was determined with regard to samples which were produced according to the mixture sequences of Examples 1, 2 and 3. A comparison was made with samples which were based on an arbitrary mixture sequence of the individual herb extracts. The results of the measurements are displayed in FIGS. 1 (arbitrary mixture sequence, without pre-mixture) and 2 (mixture sequences according to the invention). As can be seen from FIG. 2, the mixture sequence prevents the formation of crystals of the ingredients (secondary plant substances) of the herb extracts.

The crystal formation was examined microscopically, wherein the measurements took place after 2 and respectively 6 weeks' storage. The results are displayed in Tables 1 and 2.

TABLE 1

| 2 weeks' storage at room temperature | | |
|---|---|---|
| Example 1 | Example 2 | Example 3 |
| Sediment light, dark, powdery; supernatant colloidal, very turbid; uniform particles of approx. 2 µm, isolated small crystals up to 2 µm | Sediment thin, dark, powdery; supernatant colloidal, very turbid; uniform particles of approx. 2 µm, partly agglomerated; isolated small crystals approx. 1 µm | Sediment thin, dark, powdery; supernatant colloidal, very turbid; uniform particles of approx. 2 µm, a few agglomerated; small crystals |

TABLE 2

| 6 weeks' storage at room temperature | | |
|---|---|---|
| Example 1 | Example 2 | Example 3 |
| Sediment light, dark, powdery; supernatant colloidal, slightly turbid; sediment of uniform particles, connected in a gel-like manner, of approx. 2 µm, several small crystals up to 4 µm | Sediment light, dark, powdery; supernatant colloidal, slightly turbid; uniform particles of approx. 2 µm, partly agglomerated in a mucous-like manner, isolated small crystals approx. 1 µm, a few up to 2 µm | Sediment light, dark, powdery; supernatant weakly colloidal, scarcely turbid; uniform particles of approx. 2 µm, a few agglomerated, several quite small crystals 1 µm, a few needles up to 2 µm |

The foregoing disclosure of specific embodiments is intended to be illustrative of the broad concepts comprehended by the invention.

The invention claimed is:

1. The method for the production of a plant-based medicament which contains *Iberis amara*, Menthae piperitae folium, Matricariae flos, Carvi fructus, Melissae folium, Angelicae radix, Liquiritiae radix, Cardui mariae fructus and Chelidonii herba in the form of alcoholic extracts, characterized in that in a first step a) Angelicae radix extract and Liquiritiae radix extract are mixed together in a volume ratio of 1:6 to 3:1 and subsequently in at least one further step the mixture of step a) is mixed together with the extracts of the further ingredients or mixtures containing them, which are produced separately and if applicable contains additional Liquiritiae radix.

2. The method for the production of a plant-based medicament according to claim 1, characterized in that in a step b) a mixture containing extracts of Matricariae flos, *Iberis amara* and Carvi fructus is produced, the mixture of step a) is added thereto and in a step c) extracts of Cardui mariae fructus, Menthae piperitae folium, Mellissae folium and Chelidonii herba are added.

3. The method for the production of a plant-based medicament according to claim 1, characterized in that mixtures containing extracts of Menthae piperitae folium, Carvi fructus and Melissae folium; Cardui mariae fructus and Matricariae flos; and *Iberis amara* and Chelidonii herba are produced separately.

4. The method for the production of a plant-based medicament according to claim 1, characterized in that Angelicae radix extract and Liquiritiae radix extract are mixed together in step a) in a volume ratio of 1:2 to 2:1.

5. The method for the production of a plant-based medicament according to claim 1, characterized in that Angelicae radix extract and Liquiritiae radix extract are mixed together in step a) in a volume ratio of 1:1.

6. The method for the production of a plant-based medicament according to claim 3, characterized in that in a step b) the mixture of step a) is mixed together with a mixture containing extracts of Menthae piperitae folium, Carvi fructus and Melissae folium, in a step c) a mixture containing extracts of Cardui mariae fructus and Matricariae flos is added and in a step d) the addition of a mixture containing extracts of *Iberis amara* and Chelidonii herba takes place.

7. The method for the production of a plant-based medicament according to claim 3, characterized in that in a step b) the mixture of step a) is mixed together with a mixture containing extracts of Menthae piperitae folium, Carvi fructus and Melissae folium, in a step c) a mixture containing extracts of Cardui mariae fructus and Matricariae flos and a mixture containing extracts of *Iberis amara* and Chelidonii herba are mixed together and in a step d) the mixtures of the steps b) and c) are mixed together.

8. The method for the production of a plant-based medicament according to claim 3, characterized in that the mixture containing Menthae piperitae folium extract, Carvi fructus extract and Melissae folium extract contains additional Liquiritiae radix extract.

9. The method for the production of a plant-based medicament according to claim 8, characterized in that the mixture containing Menthae piperitae folium extract, Carvi fructus extract and Melissae folium extract contains additional Liquiritiae radix extract, wherein the volume of the Liquiritiae radix containing extract is in the ratio of 1:1 to the volume of Liquiritiae radix extract contained in the mixture of Angelicae radix extract and Liquiritiae radix extract of step a).

10. The method for the production of a plant-based medicament according to claim 1, which comprises
15 to 40 vol. % *Iberis amara*,
5 to 30 vol. % Menthae piperitae folium,
20 to 40 vol. % Matricariae flos,
10 to 30 vol. % Carvi fructus,
10 to 30 vol. % Melissae folium,
5 to 30 vol. % Angelicae radix,
10 to 30 vol. % Liquiritiae radix, 5 to 30 vol. % Cardui mariae fructus and
5 to 30 vol. % Chelidonii herba
in the form of alcoholic extracts.

11. The method for the production of a plant-based medicament according to claim 10, which comprises
15 vol. % *Iberis amara*,
5 vol. % Menthae piperitae folium,
20 vol. % Matricariae flos,
10 vol. % Carvi fructus,
10 vol. % Melissae folium,
10 vol. % Angelicae radix,
10 vol. % Liquiritiae radix,
10 vol. % Cardui mariae fructus and
10 vol. % Chelidonii herba
in the form of alcoholic extracts.

12. The method for the production of a plant-based medicament according to claim 1, characterized in that fresh plant extracts or drug extracts are used.

13. The method for the production of a plant-based medicament according to claim 12, characterized in that the *Iberis amara* extract is a fresh plant extract of *Iberis amara* totalis.

14. The method for the production of a plant-based medicament according to claim 13, characterized in that the *Iberis amara* extract is a fresh plant extract which has a flavonoid content of 0.05 to 0.2 mg/ml.

15. The method for the production of a plant-based medicament according to claim 13, characterized in that the *Iberis amara* extract is a fresh plant extract which has a content of cucurbitacins of 0 to 200 μg/ml.

16. The method for the production of a plant-based medicament according to claim 15, characterized in that the *Iberis amara* extract is a fresh plant extract which has a content of cucurbitacins of 35 to 185 μg/ml.

17. Method for the production of a plant-based medicament according to claim 15, characterized in that the *Iberis amara* extract is a fresh plant extract which has a content of cucurbitacin I of 0 to 100 μg/ml and a content of cucurbitacin E of 0 to 100 μg/ml.

18. The method for the production of a plant-based medicament according to claim 12, characterized in that the extracts of Menthae piperitae folium, Matricariae flos, Carvi fructus, Melissae folium, Angelicae radix, Liquiritae radix, Cardui mariae fructus and Chelidonii herba are drug extracts.

19. The method for the production of a plant-based medicament according to claim 12 or 13, characterized in that in the fresh plant extract, the ratio of macerated/percolated plant to the extract is between 1 gram:10 ml and 1 gram:1 ml.

20. The method for the production of a plant-based medicament according to claim 19, characterized in that in the fresh plant extract, the ratio of macerated/percolated plant to the extract is from 1 gram:1.5 ml to 1 gram:2.5 ml.

21. The method for the production of a plant-based medicament according to claim 12 or 18, characterized in that in the drug extracts, the ratio of the drug to the extract is from 1 gram:1 ml to 1 gram:10 ml.

22. The method for the production of a plant-based medicament according to claim 21, characterized in that in the drug extracts, the ratio of the drug to the extract is 1 gram:2 ml to 1 gram:4 ml.

23. The method for the production of a plant-based medicament according to claim 22, characterized in that in the drug extracts, the ratio of the drug to the extract is from 1 gram:2.5 ml to 1 gram:3.5 ml.

24. The method for the production of a plant-based medicament according to claim 12, characterized in that the extractant comprises an aqueous ethanol with a concentration of 0.1 to 60 vol. % ethanol.

25. The method for the production of a plant-based medicament according to claim 24, characterized in that the extractant comprises an aqueous ethanol with a concentration of 30 to 50 vol. %.

26. The method for the production of a plant-based medicament according to claim 25, characterized in that the extractant for the fresh plant extract is aqueous ethanol with a concentration of 50 vol. % ethanol, and the extractant for the drug extracts is an aqueous ethanol with a concentration of 30 vol. % ethanol.

27. A plant-based medicament produced according to the method of claim 1.

* * * * *

UNITED STATES PATENT AND TRADEMARK OFFICE
CERTIFICATE OF CORRECTION

| | | |
|---|---|---|
| PATENT NO. | : 7,985,433 B2 | Page 1 of 1 |
| APPLICATION NO. | : 12/459009 | |
| DATED | : July 26, 2011 | |
| INVENTOR(S) | : Willi Kuper and Wulf Becker | |

It is certified that error appears in the above-identified patent and that said Letters Patent is hereby corrected as shown below:

Claim 1, column 7, line 64, should read as follows:

1. A method for the production of a plant-based medica-

Signed and Sealed this
Twenty-seventh Day of September, 2011

David J. Kappos
*Director of the United States Patent and Trademark Office*